(12) United States Patent
Shen et al.

(10) Patent No.: US 7,786,098 B2
(45) Date of Patent: Aug. 31, 2010

(54) FLUOROALKOXYCOMBRETASTATIN DERIVATIVES, METHOD FOR PRODUCING THE SAME AND USE THEREOF

(75) Inventors: Weiping Shen, Shanghai (CN); Jianping Wang, Yiwu (CN); Jianguo Wang, Yiwu (CN); Hongmei Jin, Shanghai (CN); Feng Qian, Shanghai (CN); Fei Wang, Shanghai (CN)

(73) Assignee: Zhejiang Dade Pharmaceutical Group Co. Ltd., Yiwa (CN)

( * ) Notice: Subject to any disclaimer, the term of this patent is extended or adjusted under 35 U.S.C. 154(b) by 163 days.

(21) Appl. No.: 12/088,984

(22) PCT Filed: Nov. 22, 2006

(86) PCT No.: PCT/CN2006/003149

§ 371 (c)(1),
(2), (4) Date: Apr. 2, 2008

(87) PCT Pub. No.: WO2007/140662

PCT Pub. Date: Dec. 13, 2007

(65) Prior Publication Data

US 2008/0306027 A1     Dec. 11, 2008

(30) Foreign Application Priority Data

Jun. 6, 2006    (CN)    .................. 2006 1 0027307

(51) Int. Cl.
*A61K 31/661*    (2006.01)
*A61K 31/085*    (2006.01)
*A61K 31/164*    (2006.01)
*A61K 31/136*    (2006.01)
*A61P 35/00*    (2006.01)
*C07C 43/205*    (2006.01)
*C07C 211/43*    (2006.01)
*C07C 237/00*    (2006.01)
*C07F 9/06*    (2006.01)

(52) U.S. Cl. .................. 514/130; 514/626; 514/646; 514/719; 562/23; 564/442; 564/193; 568/645

(58) Field of Classification Search .................. 514/130, 514/719, 464, 626; 562/626; 564/193, 442; 568/645
See application file for complete search history.

(56) References Cited

FOREIGN PATENT DOCUMENTS

| GB | 2 403 949 A | 1/2005 |
|---|---|---|
| JP | 8-301831 A | 11/1996 |
| WO | WO 2006/036743 A2 | 4/2006 |

OTHER PUBLICATIONS

R. Munns, Plant, Cell and Environment, 2002, vol. 25, p. 239-250.*
Lawrence et al. "Synthesis and anticancer activity of fluorinated analogues of combretastatin A-4" Journal of Fluorine Chemistry vol. 123, (2003), p. 101-108, Abstract.
International Search Report, dated Mar. 8, 2007.

* cited by examiner

*Primary Examiner*—Yong Chu
(74) *Attorney, Agent, or Firm*—Hamre, Schumann, Mueller & Larson, P.C.

(57) ABSTRACT

Combretastatin derivatives of formula (I), preparation and use thereof are disclosed, wherein: $R_f$ is alkyl with 1-8 carbon atoms and 1-17 fluorine atoms, R is amino, substituted amino, hydroxyl, nitro, halo, alkyloxy, phosphate or amino acid side chain. Said derivatives have a capability to inhibit the polymerization of microtubules and are useful in treatment against tumor and neovascularization.

10 Claims, 4 Drawing Sheets

Figure 1:
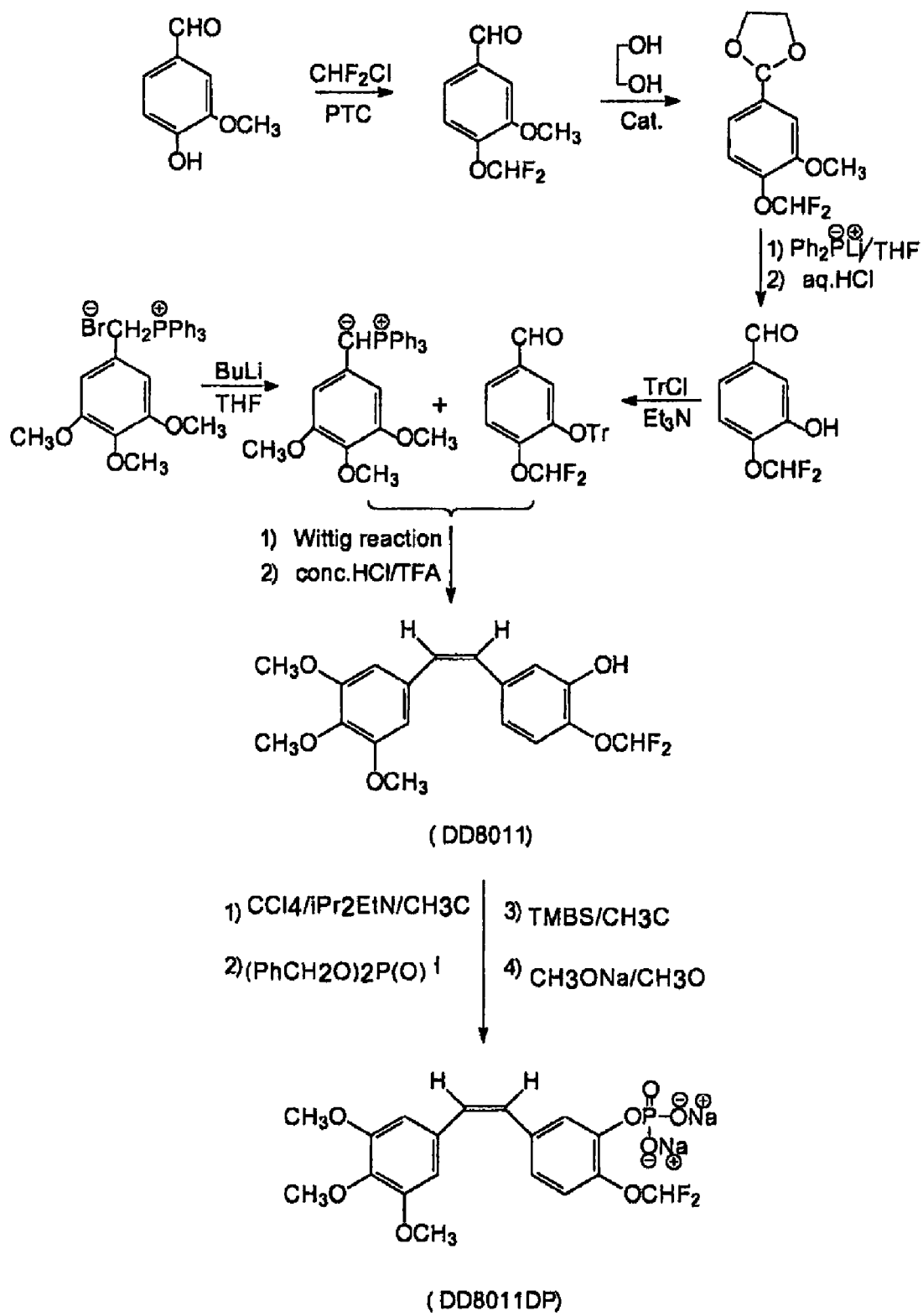

FLUOROALKOXYCOMBRETASTATIN DERIVATIVES, METHOD FOR PRODUCING THE SAME AND USE THEREOF

FIELD OF THE INVENTION

The present invention is directed to the field of pharmaceutical synthesis, especially to the synthesis of anti-cancer medicament.

BACKGROUND ARTS

In the present world, cancer is a disease showing the highest incidence and mortality rate. It seriously threatens the health of human beings and their life, and remains a puzzle for researchers. In the early 1970s, scientists knew nothing about the cause of formation of cancers. They had to find anticancer remedies blindly. In 1966, National Cancer Institute began to fund the chemical drug screening project. Thousands upon thousands of chemicals which might have the potential of treating cancer were tested one by one. As a result, many chemotherapy drugs were developed, such as, amino methyl folic acid, cyclophosphamide, cisplatin, fluorouracil, pacilitaxel etc. Though this kind of cytotoxic drugs can ameliorate or eliminate some pathological symptoms of the disease, continuous treatment usually causes serious multi-rug resistance, leading to less curative effect on treatment. What make things worse is that the cancer will develop resistance to these kinds of drugs, and then future treatment may be impossible.

In 1971, Dr. Folkman put forward the angiogenesis theory at the first time. He made the following bold hypothesis: 1) Tumor growth depends upon angiogenesis, 2) Tumor can stimulate the formation of this kind of blood vessel initiatively, 3) Tumor can secrete some chemical substance which can lure the blood vessel to grow towards the tumor, and to grow the branches. The growth of the solid tumor depends on the quantity of neoplastic cells and endothelial cells of tumour blood vessel. These two kinds of cells depend on each other for mutual existence. The fluctuation of the quantity of any kind of cells can inevitably cause the corresponding fluctuation of another one. Hence, any drug which can inhibit either neoplastic cells or endothelial cells of tumour blood vessel is useful in the treatment of cancers. Inhibiting neoplastic cells is chemotherapy using mostly cytotoxic drugs, and inhibiting endothelial cells is anti-angiogenic therapy which is the most noticeable one lately. According to the hypothesis of Dr. Folkman, the growth and transfer of solid tumor relies on the neovascularization. So, if the formation of tumor blood vessel is inhibited, then tumor cells will die because of lacking of blood and oxygen supply; and sequentially, the tumor's growth is retarded and the transfer of the tumor is inhibited. Now it was proved that angiogenesis of new blood vessels, is a requirement for a tumor to grow. A tumor having a volume of less than 1-2 mm$^3$ can survive through obtaining nutrition from the surrounding tissues by osmosis. The tumor grows slowly at that time because its further development must rely on angiogenesis to obtain sufficient nutrition. Tumor angiogenesis is a dynamic multi-step process, which involves retraction of pericytes from the abluminal surface of the capillary, release of proteases from the activated endothelial cells, degradation of the extracellular matrix (ECM) surrounding the pre-existing vessels, endothelial cell migration toward an angiogenic stimulus and their proliferation, formation of tube-like structures, fusion of the formed vessels and initiation of blood flow. This process is regulated by both the internal secretion factor of basement nerve and growth factors expressed by tumor cells and tumor matrix cells.

Anti-angiogenic therapy attacks similar vascular endothelial cells that surround different tumors. Except for the higher proliferation rate of tumor vascular endothelial cells, there is no apparent difference between them and normal ones. Normal vascular endothelial cells have longer lifetime and more stable genotype. Except for the nerve cells, endothelial cell is one kind of the cells that have the longest lifetime. Among the endothelial cells in the adulthood vascular wall, only around 0.01% of them are in the state of division. Tumor vascular endothelial cell differs from normal vascular endothelial cell in several ways. Tumor vascular endothelial cell has a proliferation rate that is on average 50-fold higher than normal vascular endothelial cell and is therefore less mature. Consequently, vascular inhibitory factors have relative specificity for tumor blood vessels, while no noticeable effect on the vascular of normal tissues. Compared with traditional chemotherapy, which directly targets tumor cells, anti-angiogenic therapy has some significant advantages: 1) Anti-angiogenic drugs have good specificity because angiogenesis is initiated once tumor occurs. Anti-angiogenic drugs directly targets neovascular endothelial cells, therefore, thousands of tumor cells will die due to lack of oxygen as long as any one of vessels that causes occlusion is destroyed. Related studies show that 99% of tumor cells die in ischemic site after two hours treated by anti-angiogenic drugs. 2) Because the vascular endothelial cells are exposed themselves to the blood flow, they can be targeted by the drugs directly. The anti-angiogenic drugs will not kill the tumor cells directly and will just change the formation and growth rate of the cells. The therapeutic dosage of the anti-angiogenic drugs is so small that is only $\frac{1}{10}$-$\frac{1}{100}$ of maximum tolerated dose (MTD). Because of the high therapeutic effectiveness with small dosage, no adverse effects are aroused as those by radiotherapy and chemotherapy. 3) The endothelial cells have relatively stable gene expressing and are not easy to produce drug resistance. The proliferation rate of the vascular endothelial cells is quicker several tens times than that of the normal tissues. Angiogenesis inhibitors have the selective effects on the tumor vascular endothelial cells, which proliferate speedily, and have very limited effects on the normal tissues. The angiogenesis inhibitors have great advantages.

The combretaceae family of shrubs and trees, found in tropical or subtropical areas, is well represented in traditional medical practices. There are 25 known combretum genera used for treating Hansen's disease and cancers in Africa and India. In the end of 1970s, after widespread screening, National Cancer Institute found that combretum genera plants can strongly inhibit the P388 lymphocytic leukemial cell. From the beginning of 1980s, there was a wide interest in studying this kind of plant. During this period, Dr. G Robert Pettit., the director of Cancer Research Institute of Arizona State University, and his colleagues isolated combretastatins from the African willow tree *Combretum caffrum* which has been used by the Zulus as herbal remedies and as paint for spears. In the *Journal of Canadian Chemistry* Dr. George R. Pettit stated that the bark of the tree had anti-tumor activity. Afterward, not only many compounds having high activity are isolated and identified, but also the research on their pharmacological mechanism and modifications of their structures have been developed. The group of Dr. Pettit firstly began an in-depth study in this field. This group studies the combretum genera plants, which resulted in isolation of a series of active phenanthrenes, stilbenes, and bibenzyls. Discovery of the very potent cell growth and tubulin inhibitors combretastatins A-1 and A-4 (hereinafter referring to CA-4 and CA-1, represented by formula II) was especially important. Both proved to be exceptionally strong inhibitors of tubulin polymerization (U.S. Pat. No. 5,561,122; WO 9935150).

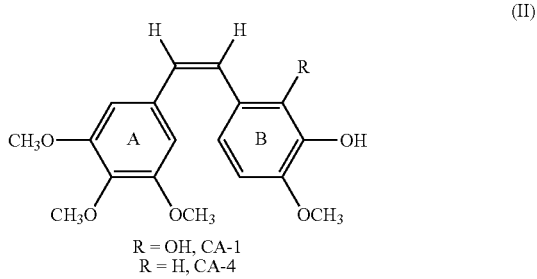

R = OH, CA-1
R = H, CA-4

There is extraordinary interest in studying the Combretastatins, though it was not so long before it was discovered. It is not only because they have higher anti-tumor activity, but also because they are small natural products which inhibit tubulin polymerization and angiogenesis. The study of the mechanism of action of the CA-4 shows that the A-ring and B-ring bind to α-tubulin and β-tubulin respectively, which cause the collapse of endothelial cells of tumor vascular. CA-4 suppresses tumor growth by attacking new-born blood vessel via inhibiting tubulin polymerization, because the blood vessels supply necessary oxygen and nutrients for tumor growth.

CA-4 can enter the endothelial cells that line the blood vessels of tumor cells. In tumours, these cells are immature and thus particularly sensitive to Combretastatins effects compared to the endothelial cells in normal tissue. Once entering the endothelial cells, Combretastatins destroys the internal skeleton of the cells and changes their shape from flat to round, effectively plugging the capillaries that feed the tumours, resulting in big area of tumor ischemia, sequentially, resulting in tumor regression. According to the experiences of prevenient experiments and clinical trials, no any traditional anticancer drug can enter this site so far. This theory was proven in the CA-4 phase I clinical trial so far. For every individual cancer patient, within 4 to 6 hours after the treatment of CA-4, the blood flow decreased obviously, and more than 95% tumor cells died. In addition to development of CA-4 as a systemic agent for the treatment of cancer, it is also being developed as a topical application for use in the treatment of various ocular diseases, including age-related macular degeneration and proliferative diabetic retinopathy. CA-4 may also have potential for the treatment of psoriasis and arthritis. CA-4 also shows effect in boosting immunity, so it may be also useful in the treatment of diseases related to AIDS (WO02058535; U.S. Pat. No. 6,773,702).

Recently, CA-4 shows exciting property in shutting down tumor vasculature as a tumor vascular targeting agent. (Thorpe P E. Clin Cancer Res. 2004 Jan. 15, 10(2):415-27; West C M, Price P. Anticancer Drugs. 2004 Mar. 15(3):179-87; Young S L, Chaplin D J. Expert Opin Investig Drugs. 2004 Sep. 13(9): 1171-82.) So developing new CA-4 analogs is becoming a highlighted subject. For example, Oxigene Inc. has developed a series of functionalized stilbene derivatives (U.S. Pat. No. 6,919,324).

It is well known that introducing fluorine to a bio-active molecule will change its biological activity, but it is uncertainty whether it will result in increase or decrease of activity. For example, the fluorocombretastain synthesized by Sigma-Tau Industrie Farmaceutiche Riunite S.P.A, which was introduced one or two fluorine atoms in the double-bond bridge, showed no any difference from CA-4 in activity.

Therefore, finding new Combretastain derivatives with higher activity is an exigent task for us.

SUMMARY OF THE INVENTION

The object of the invention is to provide fluoroalkoxycombretastatin derivatives of formula I. Another object of the invention is to provide a method for producing the compounds of formula I.

The third object of the invention is to provide a pharmaceutical composition which contains the compounds of formula I.

The forth object of the invention is to provide the medical use of the compounds of formula I.

In the first aspect, the invention provides a compounds of formula I:

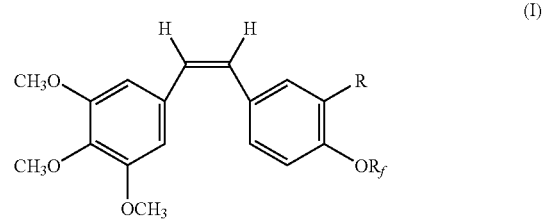

Wherein:

$R_f$ is an alkyl group having 1 to 8 carbon atoms in which 1 to 17 hydrogen atoms being substituted by 1 to 17 fluorine atoms;

R is amino, substituted amino, hydroxyl, nitro, halogen, alkoxy, phosphate or side chain of an amino acid, and its pharmaceutically acceptable salts.

preferably, $R_f$=—$CH_2F$, —$CHF_2$, —$C_nF_{2n+1}$, —$CH_2C_nF_{2n+1}$, —$CHFC_nF_{2n+1}$ or —$CH_2CHFC_nF_{2n+1}$, n is an integer of 1 to 3.

In a preferred embodiment, $R_f$ and R are selected from the following groups consisting of:

(a) $R_f$ is fluoromethyl, R is hydroxyl;
(b) $R_f$ is fluoromethyl, R is amino or substituted amino;
(c) $R_f$ is fluoromethyl, R is disodium phosphate or ammonium phosphate or internal salt of phosphorylcholine; or
(d) $R_f$ is fluoromethyl, R is —NH(COCHR'NH)m—H, R' is hydrogen, side chain of a nature amino acid, phenyl, m is an integer of 1 to 3.

In another preferred embodiment, $R_f$ and R are selected from the following groups consisting of:

(a) $R_f$ is fluoroethyl, R is hydroxyl;
(b) $R_f$ is fluoroethyl, R is amino or substituted amino;
(c) $R_f$ is fluoroethyl, R is disodium phosphate or ammonium phosphate or internal salt of phosphorylcholine; or
(d) $R_f$ is fluoroethyl, R is —NH(COCHR'NH)m—H, R' is hydrogen, side chain of a nature amino acid, phenyl, m is an integer of 1 to 3.

In another preferred embodiment, $R_f$ and R are selected from the following groups consisting of:

(a) $R_f$=—$CH_2F$, —$CHF_2$, —$CF_3$, —$CH_2CF_3$, —$CH_2CHF_2$ or —$CF_2CF_3$, R=—OH or —$OPO_3Na_2$;

or (b) $R_f$=—CH$_2$F, —CHF$_2$, —CF$_3$, —CH$_2$CF$_3$, —CH$_2$CHF$_2$ or —CF$_2$CF$_3$, R=—NH$_2$ or —NHCOCH(NH$_2$)CH$_2$OH.

In another preferred embodiment, $R_f$=—CHF$_2$, R=—OH.

In another preferred embodiment, $R_f$=—CHF$_2$, R=—OPO$_3$Na$_2$.

In another preferred embodiment, $R_f$=—CHF$_2$, R=—NH$_2$.

In another preferred embodiment, $R_f$=—CHF$_2$, R=—NHCOCH(NH$_2$)CH$_2$OH.

In another preferred embodiment, $R_f$=—CH$_2$CF$_3$, R=—OH.

In another preferred embodiment, $R_f$=—CH$_2$CF$_3$, R=—OPO$_3$Na$_2$.

In another preferred embodiment, $R_f$=—CH$_2$CF$_3$, R=—NH$_2$.

In another preferred embodiment, $R_f$=—CH$_2$CF$_3$, R=—NHCOCH(NH$_2$)CH$_2$OH.

In the second aspect, the invention provides a method for preparing the compounds of formula I, comprising the steps of:

(1) Under phase-transfer catalyst conditions, 4-hydroxy-3-methoxybenzaldehyde III is fluoroalkylated with fluorine-containing reagent to synthesize 4-fluoroalkoxy-3-methoxybenzaldehyde represented by formula V;

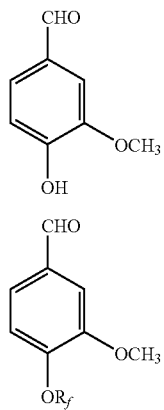

(2) By using lithium diphenylphosphine, 4-fluoroalkoxy-3-methoxybenzaldehyde V is demethylated to synthesize 4-fluoroalkoxy-3-hydroxybenzaldehyde represented by formula VI;

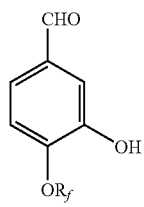

(3) The hydroxyl of 4-fluoroalkoxy-3-hydroxybenzaldehyde VI is protected, then the hydroxyl-protected 4-fluoroalkoxy-3-hydroxybenzaldehyde VI is reacted with 3,4,5-trirethoxybenzyltriphenylphosphonium ylid via Wittig reaction, and the resulted compound is released from protection to obtain the compounds of formula I.

In another preferred embodiment, the method comprises the steps of:

(a) Under phase-transfer catalyst conditions, 4-hydroxybenzaldehyde IV is fluoroalkylated with fluorine-containing reagent to synthesize 4-fluoroalkoxybenzaldehyde represented by formula VII;

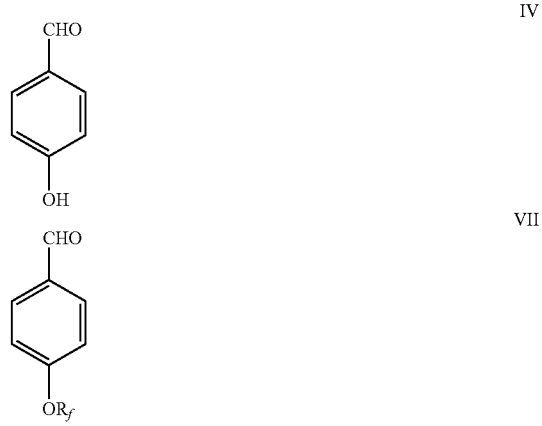

(b) 4-Fluoroalkoxybenzaldehyde VII is nitrated in 3 position of phenyl ring with nitric acid and acetic anhydride to synthesize 4-fluoroalkoxy-3-nitrobenzaldehyde represented by formula VIII;

(c) 4-fluoroalkoxy-3-nitrobenzaldehyde VIII is reacted with 3,4,5-trimethoxybenzyltriphenylphosphine ylid via Wittig reaction to obtain the compounds of formula I.

In another preferred embodiment, the said fluorine-containing reagent is fluorohalomethane or fluoroalkyl sulphonate.

In the third aspect, the invention provides a pharmaceutical composition comprising an effective amount of the compounds of formula I and pharmaceutically acceptable carrier.

In another preferred embodiment, the said pharmaceutical compositions can be administered orally or intravenously through the following medicament forms: freeze-dried powder, powder, granule, tablets, capsule, syrup, suppository, injection, emulsion, tincture, suspension, or solution.

In the forth aspect, the invention provides the use of the compounds of formula I for the manufacturing of a tubulin-binding inhibitor.

In the fifth aspect, the invention provides the use of the compounds of formula I for the manufacturing of a medicament for the treatment of the diseases caused by abnormal angiogenesis.

In another preferred embodiment, the compounds of formula I are used to treat various tumors growth and metastasis caused by abnormal angiogenesis. Said tumors include, but not limited to the following:

lung carcinoma, non small cell lung carcinoma, hepatocarcinoma, adenocarcinoma of pancreas, carcinoma of stomach, osteocarcinoma, esophagus carcinoma, breast cancer, prostate cancer, testicular tumor, colon carcinoma, ovarian cancer, bladder carcinoma, cervical cancer, melanocarcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, cystocarcinoma, medullary carcinoma, bronchogenic carcinoma, osteocyte carcinoma, epithelial carcinoma, bile duct carcinoma, embryonal carcinoma, choriocarcinoma, seminoma, Wilms' tumor, oligodendroglioma, astrocytoma, medulloblastoma, craniopharyngioma, ependymoma, pinealoma, hemangioblastoma, acoustic neuroma, meningioma, neuroblastoma, optic nerve blastoma, retinoblastoma, neurofibroma, fibrosarcoma, fibroblastoma, fibroma, fibroadenoma, fibrochondroma, fibrocystoma, fibromyxoma, fibroostroma, fibromyxosarcoma, fibropapilloma, myxosarcoma, bursal tumor, myxoenchondroma, myxochondeosarcoma, myxochondrofibrosarcoma, myxoadenoma, myxoblastoma, liposarcoma, lipoma, lipoadenoma, lipoblsst tumor, lipochondroma, lipid fibroma, lipoangioma, myxolipoma, chondrosarcoma, chondroma, chonfromyoma, chordoma, chorioadenoma, chorio-epithelioma, chorioblastoma, osteosarcoma, osteoblastic sarcoma, ostrochondrofibroma, osteochondrosarcoma, osteochondroma, osteocystoma, osteodentinoma, osteofibroma, fibrosarcoma of bone, angiosarcoma, angioma, angiolipoma, hematal chondroma, angioblastoma, angiokeratoma, angioglioma, hemangioendothelioma, hemangiofibroma, angiomyoma, angiolipoma, hematal lymphangioma, angiolipoleiomyoma, angiomyoliopma, hematal myoneuroma, hematal myxoma, angioreticuloendothelioma, lymphangiosarcoma, lymphogranulomatosis, lymphangioma, lymphoma, lymphomyxoma, lymphosarcoma, lymphangiofibroma, lymphocytoma, lymphoepithelioma, lymphoblastoma, endothelial carcinoma, endoblastoma, synovioma, synoviosarcoma, mesothelioma, mesocytoma, Ewing's tumor, liomyoma, leiomyosarcoma, leiomyoblastoma, liomyofibroma, rhabdomyoma, rhabdomyosarcoma, rhabdomyomyxoma, acute lymphocytic leukemia, acute myelocytic leukemia (myeloblastic, promyclocytic, myelomonocytic, monocytic and erythroleukemia), chronic leukemia (chronic myelocytic [granulocytic] leukemia and chronic lymphocytic leukemia), polycythemia vera, lymphoma (Hodgkin's disease and non-Hodgkin's disease), multiple myeloma.

In another preferred embodiment, the compounds of formula I are used to treat other related diseases which are aroused by pathological angiogenesis, which include but not limited to the following: rheumatoid arthritis, diabetic retinopathy, retinopathy of prematurity, retinal vein obstruction, psoriasis, acne rosacea, Kaposi sarcoma, atopic keratitis, epidemic keratoconjunctivitis, neovascular glaucoma, bacterial ulcers, fungal ulcers, Herpes simplex infections, Herpes zoster infections, protozoan infections, Mycobacterium infections, polyarteritis, sarcoidosis, scleritis, flush, Sjogren's disease, systemic lupus, Acquired Immune Deficiency Syndrome (AIDS), syphilis.

Hereby, the present invention provides some new derivatives of Combretastins with improved biological activities.

ILLUSTRATION

Figure 2:
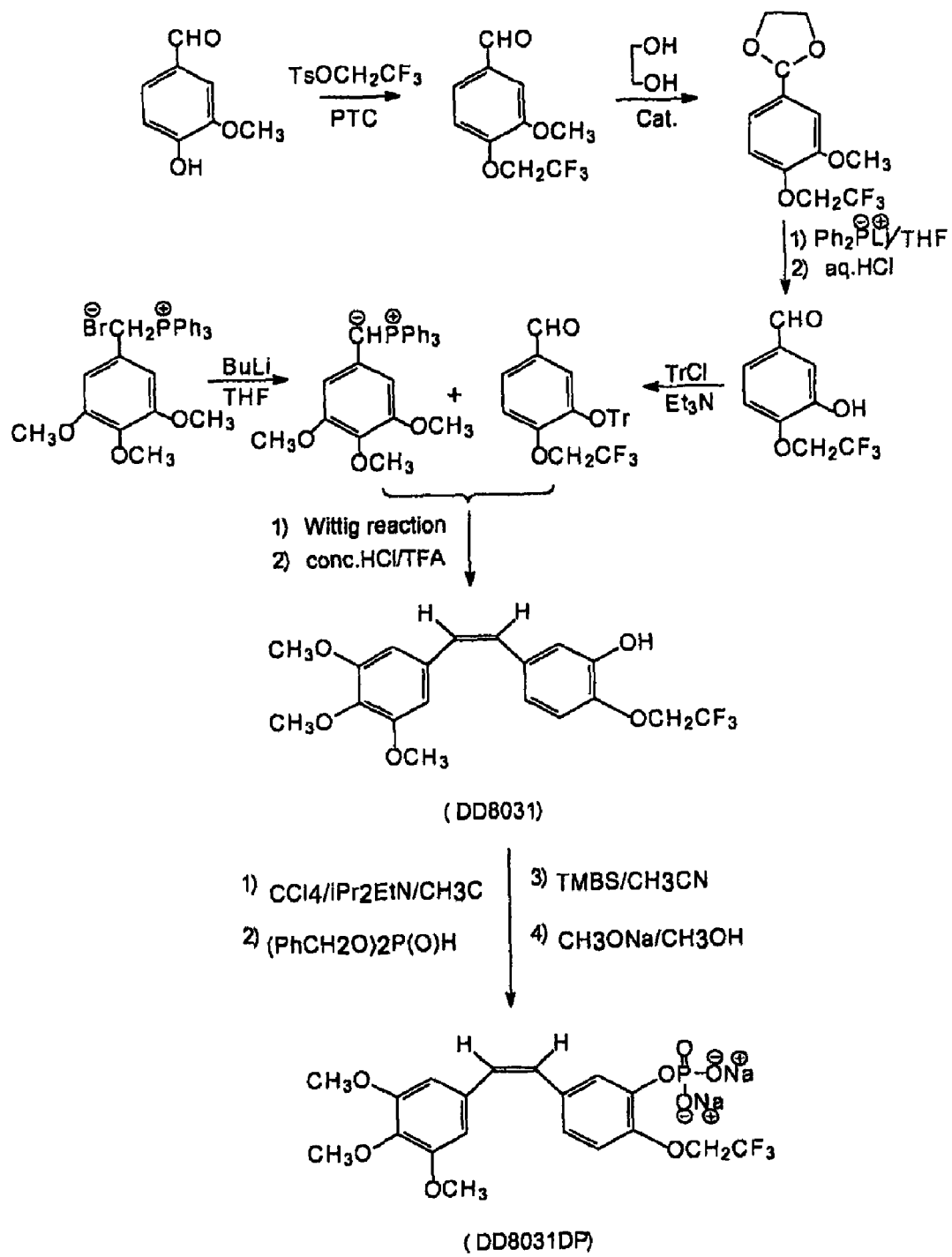
Figure 3:
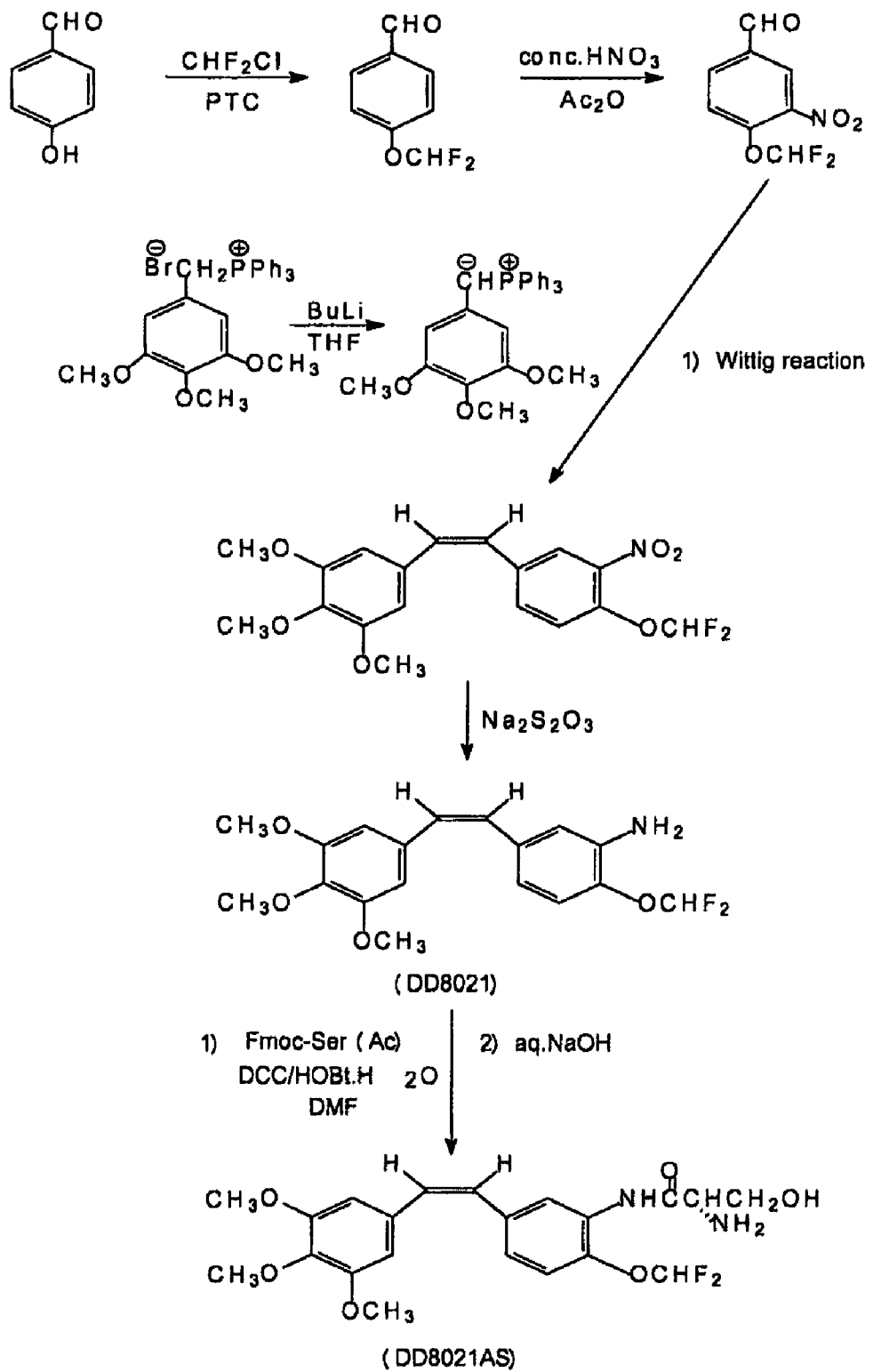
Figure 4:
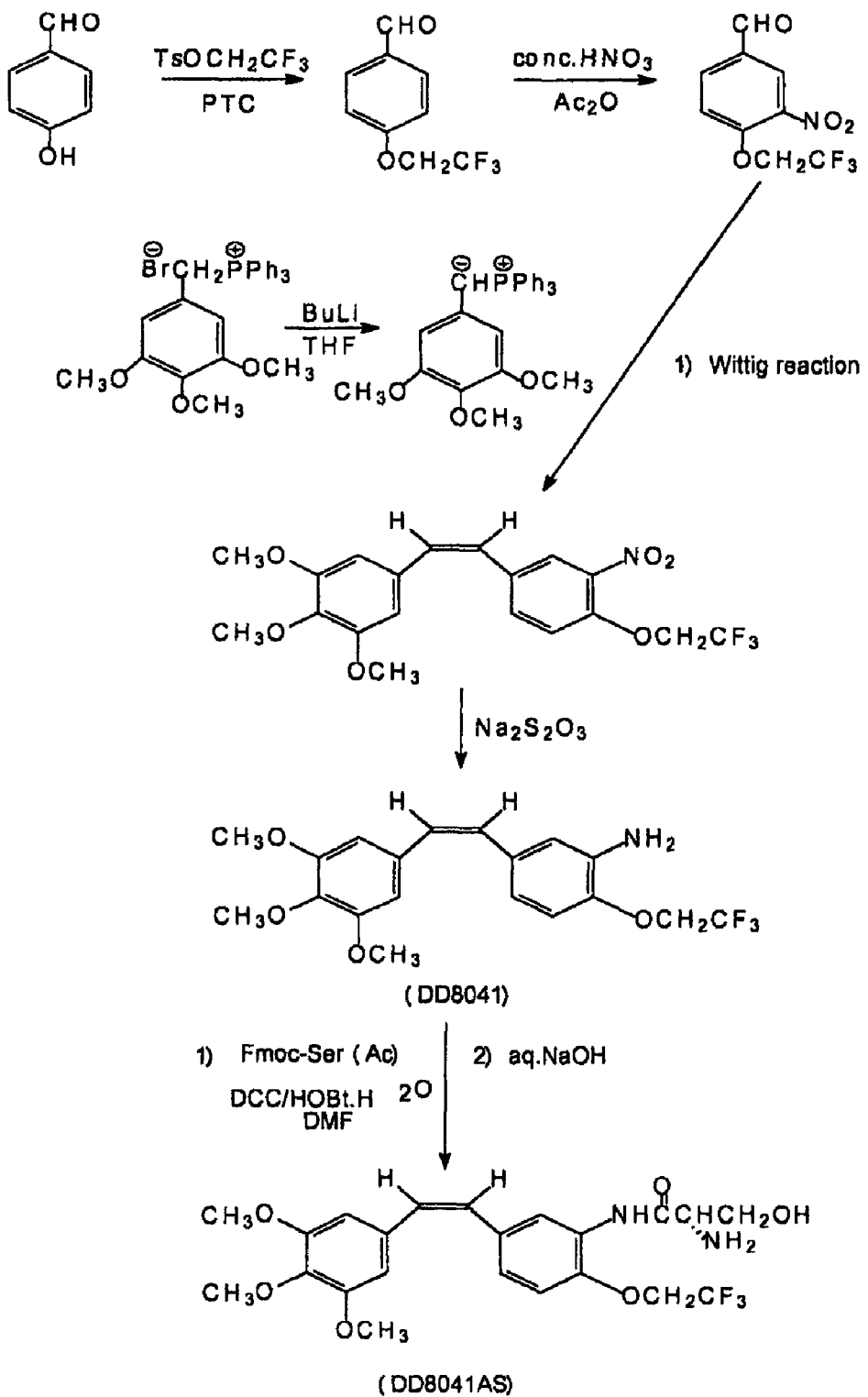

FIG. 1: synthetic route of fluoromethoxycombretastatin;
FIG. 2: synthetic route of fluoroethoxycombretastatin;
FIG. 3: synthetic route of fluoromethoxycombretastin aminoacid derivatives;
FIG. 4: synthetic route of fluoroethoxycombrestastin aminoacid derivatives.

wherein:
PTC representsphase-transfer catalyst; Cat. Represents catalyst; Wittig reaction; Ph$_2$PLi represents Lithium diphenylphosphine; THF represents tetrahydrofuran; TFA represents trifluoroacetic acid; iPr$_2$EtN represents diisopropylethylamine; (PhCH$_2$)$_2$P(O)H represents dibenzyl phosphate; TMBS represents trimethylbromosilane; Fmoc-Ser(Ac) represents N-α-9-fluorenylmethoxycarbonyl serine derivative; DCC represents cyclohexylcarbodiimide; HOBt represents 1-hydroxybenzotriazole; DMF represents dimethylformamide;

aq. HCl represents a thin hydrochloric acid aqueous solution; aq. NaOH represents a thin sodium hydroxide aqueous solution; conc. HCl represents concentrated hydrochloric acid; conc. HNO$_3$ represents concentrated nitric acid.

DETAILED DESCRIPTION OF THE INVENTION

Through extensive and intensive study, the inventors unexpectedly discovered that the 4' position of B-ring of the nature product Combretastatin is an active site, and that a fluoroalkoxy group can be introduced in this site to improve the targeting activity of tumor vascular.

The above mentioned nature product Combretastatin was successfully introduced a fluoroalkoxy group in the 4' position of B aromatic ring by means of the key reaction of demethylation using lithium diphenylphosphine selectively.

Comparing with CA-4, these new compounds of formula I enhance the inhibition of tubulin polymerization, which can be used for treating a pathological state caused by abnormal angiogenesis.

As referred herein, the derivatives of Combretastatin are compounds represented by formula II Compounds The present invention provided new derivatives of Combretastatin in which 4' position of B aromatic ring was introduced a fluoroalkoxy group, represented by Formula I

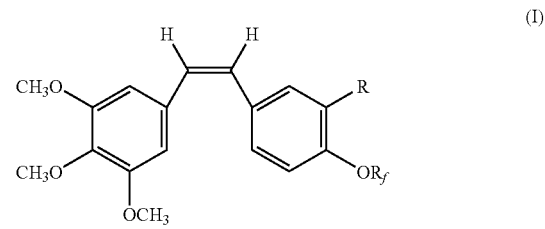

Wherein,

R$_f$ is an alkyl group having 1 to 8 carbon atoms in which 1 to 17 hydrogen atoms being substituted by 1 to 17 fluorine atoms;

R is amino, substituted amino, hydroxyl, nitro, halogen, alkoxy, phosphate or side chain of an amino acid, and its pharmaceutically acceptable salts.

Preferably, $R_f$=—$CH_2F$, —$CHF_2$, —$C_nF_{2n+1}$, —$CH_2C_nF_{2n+1}$, —$CHFC_nF_{2n+1}$ or —$CH_2CHFC_nF_{2n+1}$, n is an integer of 1 to 3.

The preferred compounds of formula I in the present invention are fluoromethoxycombretastatin or fluoromethoxycombretastatin aminoacid derivatives represented by formula I, wherein $R_f$=—$CH_2F$, —$CHF_2$ or —$CF_3$, R=—OH, —$OPO_3Na_2$, —$NH_2$ or —$NHCOCH(NH_2)CH_2OH$;

Preferably, $R_f$=—$CH_2F$, R=—OH, —$OPO_3Na_2$, —$NH_2$ or —$NHCOCH(NH_2)CH_2OH$.

The another preferred compounds of formula I in the present invention are fluoroethoxycombretastatin or fluoroethoxycombretastatin aminoacid derivatives represented by formula I, wherein, $R_f$=—$CH_2CF_3$, —$CH_2CHF_2$ or —$CF_2CF_3$, R=—OH, —$OPO_3Na_2$, —$NH_2$ or —$NHCOCH(NH_2)CH_2OH$.

The fluoroalkoxycombretastatin derivatives of the present invention can form pharmaceutically acceptable base-addition salts with inorganic bases or organic bases. Said inorganic bases can include but not limited to potassium hydroxide and ammonium hydroxide, and said organic bases include, but not limited to, aliphatic amines (such as triethylamine), hydroxyamines (such as ethanol amine), aminoacids (such as histidine), aminoglycosides (such as neoamine).

The fluoroalkoxycombretastatin derivatives of the present invention can form pharmaceutically acceptable acid-addition salts with inorganic acids or organic acids. Said inorganic acids can include but not limited to hydrochloric acid, sulfuric acid and phosphoric acid, and organic acids include, but not limited to, oxalic acid, fumaric acid, maleic acid, malic acid, citric acid, tartaric acid and glutamic acid.

Preparations of Compounds

The present invention provides a process for the preparation of compounds of formula I comprising the following steps:

Under the phase transfer catalyst, 4-hydroxy-3-methoxybenzaldehyde was fluoroalkylated, then selectively demethylated into a series of novel fluorinated alkoxybenzaldehyde derivatives by using lithium diphenylphosphine; sequentially. The above compound was nitrated, reduced, hydroxy protected, and then underwent Wittig reaction, deprotection, phosphatization, combining with aminoacids etc. to obtain a series of fluoroalkoxycombretastatin derivatives.

Synthesis of Fluoroalkoxybenzaldehyde Derivatives 4-fluoroalkoxy-3-methoxybenzaldehyde (V) or 4-fluoroalkoxybenzaldehyde (VII) was prepared by 4-hydroxy-3-methoxybenzaldehyde(III) or 4-hydroxybenzaldehyde (IV) using fluoroalkylation reagent in the presence of inorganic base and phase transfer catalyst.

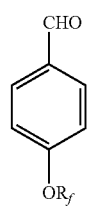

III

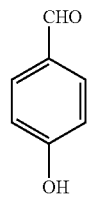

IV

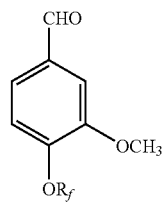

V

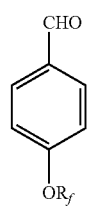

VII

Said fluoroalkylation reagents were selected from the group consisting of fluorohaloalkane, fluoroalkyl sulfonate, preferably from the group consisting of Freon (F22) or fluoroalkyl p-toluenesulfonate. Said inorganic bases were selected from the group consisting of: hydroxide, one or more of carbonates, preferably from the group consisting of potassium hydroxide and/or potassium carbonate. Said phase transfer catalyst were selected from the group consisting of quaternary ammonium salts, quaternary phosphonium salts, crown ether, polyethyleneglycol(PEG), preferably from the group consisting of benzyltriethylammonium chloride, tetrabutylammonium bisulphate(TBAB), 18-crown-6, diphenyl-18-crown-6, dicyclohexyl-18-crown-6 ethers or PEG-400.

The formyl group of 4-fluoroalkoxy-3-methoxybenzaldehyde (V) was protected by using glycol compounds, then the 3-position methoxyl was selectively demethylated with lithium diphenylphosphine to obtain 4-fluoroalkoxy-3-hydroxybenzaldehyde VI.4-Fluoroalkoxybenzaldehyde VII was nitrified in the meta-position with concentrated nitric acid in the presence of acetyl anhydride as solvent to obtain 3-nitro-4-fluoroalkoxybenzaldehyde VIII.

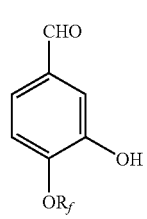

VI

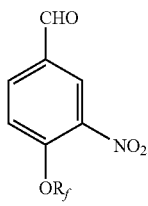

VIII

Synthesis of Fluoroalkoxycombretastatin Derivatives

In the presence of organic base catalyst, 4-fluoroalkoxy-3-hydroxybenzaldehyde VI was reacted with triphenylmethyl chloride to obtain 3-triphenymethoxy-4-fluoroalkoxybenzaldehyde.

3,4,5-trimethoxybenzyltriphenylphosphine bromide was converted into corresponding P-ylid with n-butyl lithium, then the corresponding P-ylid was reacted with the above 3-triphenymethoxy-4-fluoroalkoxybenzaldehyde via Wittig reaction to form the fluoroalkoxystilbene derivatives. Subsequently, the trityl group was deprotected with the combination action of concentrated hydrochloric acid and trifluoroacetic acid to obtain 3'-hydroxyfluoroalkoxycombretastatin derivatives IX.

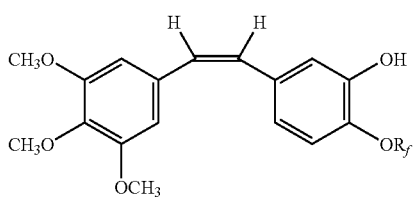

IX

Similarly, 4-fluoroalkoxy-3-nitrobenzaldehyde VIII was reacted with above P-ylid via Wittig reaction to obtain 3'-nitrofluoroalkoxycombretastatin derivatives X.

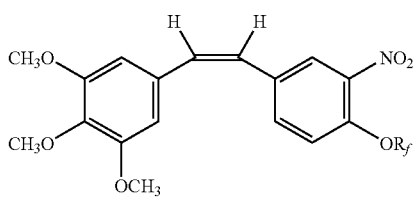

X

Synthesis of Fluoroalkoxycombretastatin Phosphate or Aminoacid Derivatives

As shown in FIG. 1 or 2, the hydroxy of 3'-position of above fluoroalkoxycombretastatin derivative IX was converted to prelate salt by carbon tetrachloride, di(isopropyl) ethylamine, dibenzyl phosphite, trimethylsilane bromide, sodium methoxide, in turn forming fluoroalkoxycombretastatin phosphate XI.

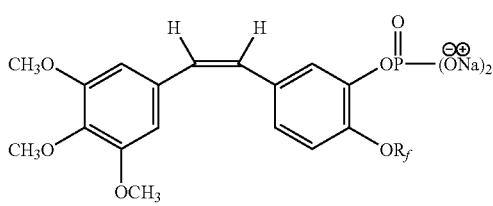

XI

Or ss shown in FIG. 3 or FIG. 4, the nitro in 3' position of the above fluoroalkoxycombretastatin derivatives X was reduced to amino by reducing agents. The preferred reducing agents were tin(II) chloride, zinc powder/acetic acid or sodium thiosulfate. Successively, the reduced product was treated with N-α-9-fluorenylmethoxycarbonyl amino acid derivative (FmocAA), cyclohexylcarbodiimide(DCC) and 1-hydroxybenzotriazole (HOBt) to introduce an amino-acid side chain in the 3-position. Subsequently, the product having an amino-acid side chain in the 3-position was deprotected with sodium hydroxide into aminocarboxamide to obtain fluoroalkoxycombretastatin aminoacid derivatives XII

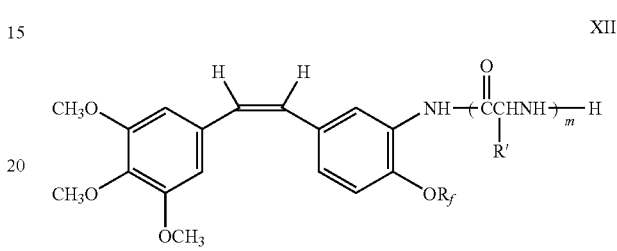

XII

Wherein, R'=H, phenyl or side chain of amino-acid, m is an integer of 1 to 3.

Pharmaceutical Compositions

The pharmaceutical composition of the invention contains therapeutic effective amount of compounds of formula I and the pharmaceutical acceptable carrier, in which the amount of the compounds of formula I is 0.1 to 99% (w/w) of the compositions. The said pharmaceutical compositions could be administered orally or intravenously by the following medicament forms: freeze-dried powder, granule, powder, tablets, capsule, syrup, suppository, injection, emulsion, tincture, suspension, or solution.

For intravenous administration, the compositions could take the form of freeze-dried powder, which was dissolved with saline or glucose solution.

For oral administration, the compositions could take the form of tablet, tincture, capsule, suppository, syrups, granule, emulsion, suspensions or solutions.

The dosage of the active ingredient varies with the way of administration and the degree of progression of the diseases. When the compound of the present invention was taken by a daily dosage from about 0.5-500 mg/kg body weight/day, it gives a satisfied treatment result. In one preferred embodiment of the present invention, the invented compound is administered to the subject in divided doses of 2 to four times or by extended-release form. For the most big mammals, the daily dosage is between 1 and 100 mg totally. The suitable oral administration dosage form contained 0.5-500 mg active ingredient, which was mixed with solid or liquid form of pharmaceutical acceptable vehicle. The dosage is adjustable for the most preferred treatment response. For example, according to the different therapeutic conditions, the invented compositions can be administrated daily in divided doses, or can be administrated scales down. Generally, the suitable clinical oral administration dosage for an adult is between 1 and 1000 mg, the preferred one is 10-200 mg. Non-oral administration dosage for an adult is between 0.1 and 100 mg, the preferred one is 1-100 mg.

The fluoroalkoxycombretastatin of the present invention which were prepared by the above-mentioned methods can be administered either orally or intravenously when it is used as vascular targeting agent. The dosage of the active ingredient varies with the degree of progression of the disease. The daily dosage is usually between 1 and 3,000 mg for an adult.

In a preferred embodiment, compounds of present invention was administered orally or intravenously. The solid carriers included starch, lactose, calcium hydrogen phosphate, crystalline cellulose, sugar and kaolin; and the liquid carriers included axenic water, polyethylene glycol, mannitol, non-ionic surfactant and edible oil (such as corn oil, peanut oil and sesame oil), which were suitable for the characteristic of the active ingredient or for the specific administration form. The adjuvant which was usually used in the preparation of the medicines was also made use of, such as flavoring, pigment, preservative and antioxidant, such as Vitamin E, Vitamin C, BHT and BHA.

As cited in the specification, intravenous administration included intraperitoneal injection and drip fluid infusion with freeze-dried powder being dissolved with saline or glucose solution. The freeze-dried powder could be prepared by the routine way in the art.

Compositions of the invention can be administered orally, which is including tablets and capsules. The preparations may be prepared by mixing the effective ingredient and at least one of pharmaceutically acceptable additives, as the additives including excipients, binders, disintegrants, lubricants, colorants, corrigents, antioxidants, preservatives and the like, and the resulting mixture is formed into powder, granules, tablets, coated tablet, pills, capsules or the like. Examples of suitable excipients include one or more of lactose, corn starch, saccharide, dextrose, sorbitol, and crystalline cellulose. Examples of suitable binders include one or more of polyvinyl alcohol, polyvinyl ether, ethyl cellulose, methyl cellulose, gum Arabic, tragacanth, gelatin, shellac, hydroxypropyl cellulose, hydroxypropyl starch, and polyvinyl pyrrolidone. Examples of typical disintegrants include one or more of starch, agar, gelatin powder, crystalline cellulose, calcium carbonate, sodium hydrogen carbonate, calcium citrate, dextran, and pectin. Examples of appropriate lubricants include one or more of magnesium stearate, talc, polyethylene glycol, silica, and hardened vegetable oil. Examples of typical colorants include colorants which have been approved for addition to medicines. Examples of acceptable corrigents include cacao powder, menthol, peppermint oil, refined borneol, and cinnamon. The tablets or granules can be coated with sugar, gelatin and etc. if necessary. The medicaments can also contain other additive, including inert diluent, preservative such as p-hydroxybenzoic esters and sorbic acid, antioxidant such as Vitamin E, Vitamin C, BHT and BHA, decomposition agent, adhesive agent, puffing agent, buffer solution, edulcorant, flavoring and perfume. Tablets and pills can also be covered with enteric coating. Examples of antioxidants include vitamin E, vitamin C, BHT and BHA. Examples of preservatives include p-hydroxybenzoic esters, sorbic acid. Tablets and granules may be coated with sugar, gelatin or the like as desired. The liquid forms of oral administration include emulsion, syrup, tincture, suspension and solution, which can contain usually used inert diluent such as water.

The main advantage of the invention is introducing fluoroalkoxy at 4' position of B aromatic ring of nature product of Combretastatin to improve its targeting activity toward tumor vascular.

The invention is further illustrated by the following examples. These examples are only intended to illustrate the invention, but not to limit the scope of the invention. For the experimental methods in the following examples, they are performed under routine conditions, or as instructed by the manufacturers, and all parts, percents, rations are by weight, unless otherwise specified.

EXAMPLE 1

Synthesis of 4-difluoromethoxybenzaldehyde

A 1-liter four-necked flask fitted with thermometer, reflux condenser, mechanical stirrer, and gas inlet was charged 50 grams (0.41 mol) of 4-hydroxybenzaldehyde and 400 ml of isopropyl alcohol. The mixture was stirred for 20 min, and then a 120 ml aqueous solution containing 5 grams of 18-crown-6 ether and 106.3 grams of sodium hydroxide (2.665 mol) water was dropped thereto. After dropping, the mixture was stirred for 30 min., then heated to 65° C., and then chlorodifluoromethane was introduced through the inlet within 5-6 hrs, monitored with TLC. After reaction, the mixture was cooled to 15° C., and 400 ml of water was then added to quench the reaction. The resulting mixture was extracted three times with ether (3×300 ml). The organic layer was washed with water to pH=7, and dried with anhydrous magnesium sulfate. The ether was removed by flash distillation and then the residue was distilled under reduced pressure to give 4-difluoroalkoxybenzaldehye (85-87° C./10 mmHg) in a yield of 95%. $^1$H-NMR (ppm) δ: 9.87 (1H, s; —CHO); 7.70 (2H, m; 2,6-ArH); 7.36 (1H, t; $J^2_{H-F}$=68 Hz; —CHF$_2$); 6.96 (2H, m; 3,5-ArH).

EXAMPLE 2

Synthesis of 4-difluoromethoxy-3-methoxybenzaldehyde

Repeating Example 1, except that 4-hydroxybenzaldehyde was replaced with 62.5 grams (0.41 mol) of 4-hydroxy-3-methoxy-benzaldehyde to obtain 4-difluoromethoxy-3-methoxybenzaldehyde (117-120° C./10 mmHg) in a yield of 93%. $^1$H-NMR (ppm) δ: 9.85 (1H, s; —CHO); 7.38 (1H, t; $J^2_{H-F}$=69 Hz; —CHF$_2$); 7.27 (1H, m; 6-ArH); 7.20 (1H, m; 2-ArH); 6.83 (1H, m; 5-ArH); 3.73 (3H, s; —OCH$_3$).

EXAMPLE 3

Synthesis of 4-difluoromethoxy-3-hydroxybenzaldehyde

Step 1: under argon atmosphere, 61 grams (0.3 mol) of 4-difluoromethoxy-3-methoxybenzaldehyde, 130 grams (2.1 mol) of ethylene glycol and 133 grams (0.9 mol) of triethyl orthoformate were in turn charged into a three-necked flask. The mixture was heated to reflux, and then 1 ml of boron trifluoride ether solution was added as catalyst. The mixture was reacted for 24 hours, monitored with TLC. The mixture was then cooled to room temperature, and 200 ml of 15% aqueous sodium hydroxide solution was added. The mixture was extracted with 300 ml of ether. The extract was washed with saturated brine, then was dried with anhydrous magnesium sulfate, distilled under reduced pressure to give yellow oily product.

Step 2: 200 ml of 1.28M tetrahydrofuran solution of lithium diphenylphosphine was charged in a flask, 50 grams (0.2 mol) of the above-prepared acetal was added in batch. After addition, the resulting mixture was stirred for 3-4 hours under room temperature, monitored with TLC. Water was added to quench the reaction, then 200 ml of 30% aqueous sodium hydroxide solution was added. The mixture was extracted with 300 ml of ether. The water layer was cooled and acidified with hydrochloric acid to pH=3-4, and then was extracted with 500 ml of ether. The ether extracts was combined and washed with saturated brine, dried with anhydrous magnesium sulfate. The dried extract was filtrated and removed solvent under reduced pressure to provide yellow solid. The crude product was recrystallized from benzene/petroleum ether to give 31.2 grams of yellowish crystalline solid (m.p. 104-106° C.) in a yield of 83%. $^1$H-NMR (ppm) δ: 9.86 (1H, s; —CHO); 7.37 (1H, t; $J^2_{H-F}$=72 Hz; —CHF$_2$; 7.26 (1H, m; 6-ArH): 7.17 (1H, m; 2-ArH); 6.79 (1H, m; 5-ArH); 4.88 (1H, s; —OH). $^{13}$C-NMR (ppm) δ: 191.0 (CHO), 163.9 (t, CHF$_2$), 157.2 (4-ArC), 146.2 (3-ArC), 130.6 (1-ArC), 123.5 (6-ArC), 116.7 (2-ArC), 116.2 (5-ArC).

EXAMPLE 4

Synthesis of 4-difluoromethoxy-3-nitrobenzaldehyde 72 grams (0.42 mol) of p-difluoromethoxybenzaldehyde and 400 ml of acetic anhydride are charged into 1000 ml of a three-necked flask with drop funnel and mechanical stirrer. The mixture was cooled with ice-salt bath. A solution of 36 ml of concentrated nitric acid in 50 ml of dichloromethane was added dropwise at less than 5° C. within 3-4 hours. Reaction progress was monitored by TLC. The temperature was increased to room temperature and was stirred for two days.

The reaction mixture was cooled to 0-5° C. Under stirring, 20% aqueous hydrochloric acid solution was added until precipitate was formed and the mixture was further cooled till no precipitate was formed. The mixture was filtered to give yellow crystal. Re-crystallized the crude product from 95% ethanol solution to obtain 74 grams (m.p. 88-90° C.) of yellowish crystalline solid in yield of 81%. $^1$H-NMR (ppm) δ: 9.92 (1H, s; —CHO); 7.87 (1H, t; $J^2_{H-F}$=70 Hz; —CHF$_2$); 7.68 (1H, m; 6-ArH); 7.59 (1H, m; 2-ArH); 7.22 (1H, m; 5-ArH). $^{13}$C-NMR (ppm) δ: 194.0 (CHO), 165.1 (t, CHF$_2$), 160.2 (4-ArC), 157.4 (3-ArC), 137.3 (1-ArC), 130.2 (6-ArC), 122.5 (2-ArC), 120.2 (5-ArC).

EXAMPLE 5

Synthesis of 4-trifluoroethoxy-benzaldehyde 50 grams (0.41 mol) of 4-hydroxybenzaldehyde, 400 ml of N,N-dimethylformamide (DMF), and 5 grams of 18-crown-6 ether was added into a one-litre four-necked flask with thermometer, mechanical stirrer and reflux condenser, and then the mixture was stirred for 20 minutes. 168 grams (1.22 mol) of potassium carbonate powder was added in batch and stirred another 30 minutes. The reaction mixture was heated to 110° C., and then a solution of 115 gram (0.45 mol) of trifluoroethyl toluene-4-sulfonate in 100 ml DMF was added dropwise within about 1 hour. The reaction mixture was heated to 130° C. for 3-4 hours. The reaction was monitored by TLC. The mixture was cooled to 0° C. and was poured into cooled 600 ml of 3N hydrochloric acid, and was stirred. The mixture was extracted with 1000 ml of ether. The water layer was separated and extracted with ether (3×400 ml). The ether extracts were combined and washed with 400 ml of 3N hydrochloric acid, distilled water, brine in turn. Then it was dried over anhydrous magnesium sulfate. The ether was removed by flash distillation, and the residue was vacuum distilled to give 4-trifluoroethoxybenzaldehyde (95-97° C./10 mmHg) in a yield of 88%. $^1$H-NMR (ppm) δ: 9.80 (1H, s; —CHO); 7.65 (2H, m; 2,6-ArH); 6.83 (2H, m; 3,5-ArH); 4.56 (2H, q; $J^3_{H-F}$=7.2 Hz; —CH$_2$CF$_3$).

EXAMPLE 6

Synthesis of 4-trifluoroethoxy-3-methoxybenzalhyde

Repeating Example 5, except that 4-hydroxybenzaldehyde was replaced with 4-hydroxy-3-methoxy-benzaldehyde to give 4-trifluoroethoxy-3-methoxybenzaldehyde (126~129° C./10 mmHg) in a yield of 83%. $^1$H-NMR (ppm) δ: 9.88 (1H, s; —CHO); 7.27 (1H, m; 6-ArH); 7.20 (1H, m; 2-ArH); 6.83 (1H, m; 5-ArH); 4.48 (2H, q; $J^3_{H-F}$=7.2 Hz; —CH$_2$CF$_3$); 3.65 (3H, s; —OCH$_3$).

EXAMPLE 7

Synthesis of 4-trifluoroethoxy-3-hydroxybenzalhyde

Repeating Example 3, except that 4-difluoromethoxy-3-methoxybenzaldehyde was replaced with 70 grams (0.3 mol) of 4-trifluoroethoxy-3-methoxybenzaldehyde to give 4-trifluoroethoxy-3-hydroxybenzaldehyde (m.p. 133~135° C.) in a yield of 81%. $^1$H-NMR (ppm) δ: 9.81 (1H, s; —CHO); 7.26 (1H, m; 6-ArH); 7.17 (1H, m; 2-ArH); 6.79 (1H, m; 5-ArH); 4.88 (1H, s; —OH); 4.45 (2H, q; $J^3_{H-F}$=7.2 Hz; —CH$_2$CF$_3$). $^{13}$C-NMR (ppm)) δ: 191.0 (CHO), 157.2 (4-ArC), 146.2 (3-ArC), 130.6 (1-ArC), 126 (q, CF$_3$), 123.5 (6-ArC), 116.7 (2-ArC), 116.2 (5-ArC), 87 (m, CH$_2$).

EXAMPLE 8

Synthesis of 4-trifluoroethoxy-3-nitrobenzalhyde

Repeating Example 4, except that 4-difluoromethoxybenzaldehyde was replaced with 86 grams (0.42 mol) of 4-trifluoroethoxybenzaldehyde to give 4-trifluoroethoxy-3-nitrobenzaldehyde (m.p. 126~127° C.) in a yield of 78%. $^1$H-NMR (ppm) δ: 9.91 (1H, s; —CHO); 7.28 (1H, m; 6-ArH); 7.20 (1H, m; 2-ArH); 6.77 (1H, m; 5-ArH); 4.46 (2H, q; $J^3_{H-F}$=7.2 Hz; —CH$_2$CF$_3$). $^{13}$C-NMR (ppm) δ: 191.0 (CHO), 157.2 (4-ArC), 146.2 (3-ArC), 130.6 (1-ArC), 127 (q, CF$_3$), 123.5 (6-ArC), 116.7 (2-ArC), 116.2 (5-ArC), 89 (m, CH$_2$).

EXAMPLE 9

Synthesis of (Z)-1-(3,4,5-trimethoxyphenyl)-2-(3'-hydroxy-4'-difluoromethoxyphenyl)-ethene (DD8011, formula XIII)

Step 1: 12.5 grams (0.066 mol) of 4-difluoromethoxy-3-hydroxybenzaldehyde and 21.1 grams (0.076 mol) of triphenylmethyl chloride was dissolved in 42 ml dried THF in 500 ml four-necked flask. The mixture is stirred uniformly. 1.3 ml of triethylamine was slowly dropped into the mixture and stirred for 1 hour after addition. The reaction was monitored by TLC. After the reaction completed, 50 ml of water was added to quench the reaction. The mixture was stirred another 30 min and 100 ml of ethyl acetate was added to dissolve the floc. 250 ml of n-heptane was added to precipitate the pale yellowish solid. The solid was filtered and was washed twice with water, and washed with a mixture of 10 ml of ethyl acetate and 20 ml of petroleum ether to give pale white crystalline solid. Then this crystalline solid is recrystallizated from ethyl acetate/petroleum ether. 25.8 grams of pale white crystalline solid in a yield of 91%. $^1$H-NMR (ppm) δ: 9.87 (s, 1H, CHO), 7.37 (t, 1H, $J^2_{H-F}$=72 Hz, —CHF$_2$), 7.26 (m, 2H, Ar—H), 7.19 (m, 15H, Tr-H), 6.85 (s, 1H, Ar—H).

Step 2: Under argon atmosphere, 15 grams (28.7 mmole) of trimethoxyphenylmethylenetriphenylphosphonium bromide was suspended in 30 ml of THF, and the mixture was cooled to about −15° C. 22 ml of an n-butyl lithium solution in hexane (approximately 1.6 mol/L) was slowly dropped, and then the reaction mixture was stirred for another 1 hour. A solution of 12.5 grams (29 mmol) of the above-prepared aldehyde in step 1 was slowly dropped in 24 ml THF. The reaction mixture was stirred over night, and the reaction temperature slowly ascended to room temperature. The reaction was monitored by TLC. The reaction mixture was cooled again to −5° C. the next day, and the brine was added to quench the reaction. The organic layer was separated and the solvent was removed by flash distillation. The crude product was purified by flash column chromatography to obtain 15 grams of white crystalline solid in a yield of 88%. $^1$H-NMR (ppm) δ: 7.19 (m, 15H, Tr-H); 6.94 (d, 1H, 2'-H); 6.80 (dd, 1H, 6'-H); 6.74 (d, 1H, 5'-H); 6.55 (s, 2H, 2,6-H); 6.52 (t, 1H; $J^2_{H-F}$=72 Hz; —CHF$_2$) 6.47 (d, 1H, 1a-H); 6.41 (d, 1H, 1a'-H); 3.88 (s, 3H, 4-OCH$_3$); 3.71 (s, 6H, 3,5-OCH$_3$).

Step 3: At room temperature, 10 grams (16.8 mmol) of above Wittig reacting compounds in step 2 was dissolved in 20 ml of toluene. 4 ml of 37% aqueous hydrochloric solution was added dropwise. The reaction was monitored by TLC. After the reaction was completed, water was added to stop the reaction. The reaction mixture was cooled to 0-5° C. to give white crystalline solid under agitation. The solid was filtered and dried to give 5.6 gram of white crystalline solid in a yield of 95%. $^1$H-NMR (ppm) δ: 7.02 (d, 1H, 2'-H); 6.94 (dd, 1H, 6'-H); 6.80 (d, 1H, 5'-H); 6.62 (s, 2H, 2,6-H); 6.53 (t, 1H; $J^2_{H-F}$=72 Hz; —CHF$_2$) 6.46 (d, 1H, 1a-H); 6.40 (d, 1H, 1a'-H); 5.51 (broad, 1H; OH); 3.86 (s, 3H, 4-OCH$_3$); 3.70 (s, 6H, 3,5-OCH$_3$).

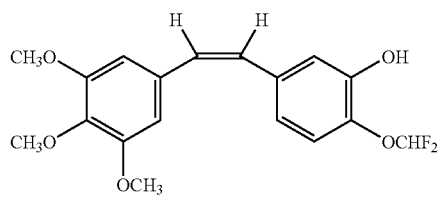

XIII

EXAMPLE 10

Synthesis of (Z)-1-(3,4,5-trimethoxyphenyl)-2-(3'-amino-4'-difluoromethoxyphenyl)-ethene (DD8021, formula XIV)

Step 1: Under argon atmosphere, 15 grams (28.7 mmole) of trimethoxyphenylmethylenetriphenylphosphonium bromide was suspended in 30 ml of THF, and the mixture was cooled to about −15° C. 22 ml of an n-butyl lithium solution in hexane (approximately 1.6 mol/L) was slowly dropped, and then the reaction mixture was stirred for another 1 hour. A solution of 6.3 grams (29 mmol) of 4-difluoromethoxy-3-nitrobenzaldehyde in 24 ml THF was slowly dropped. The reaction mixture was stirred over night, and the reaction temperature slowly ascended to room temperature. The reaction was monitored by TLC. The reaction mixture was cooled again to −5°C., and brine was added to quench the reaction. The organic layer was separated and the solvent was removed by flash distillation. The crude product was purified by flash column chromatography to obtain 6.6 grams of pale yellowish crystalline solid in a yield of 61%. $^1$H-NMR (ppm) δ: 7.32 (d, 1H, 2'-H), 7.16 (dd, 1H, 6'-H), 6.90 (d, 1H, 5'-H), 6.78 (t, 1H; $J^2_{H-F}$=72 Hz; —CHF$_2$), 6.64 (s, 2H, 2,6-H), 6.49 (d, 1H, 1a-H), 6.43 (d, 1H, 1a'-H), 3.86 (s, 3H, 4-OCH$_3$), 3.70 (s, 6H, 3,5-OCH$_3$).

Step 2: 4.1 grams (10.8 mmol) of (Z)-1-(3,4,5-trimethoxyphenyl)-2-(3'-nitro-4'-difluoromethoxy-phenyl)ethene was dissolved in 10 ml of acetone/water (V/V, 2:1). The mixture was heated to 50°C., and was stirred to dissolve all the solid. 18.8 grams of sodium thiosulphate was added and the reaction mixture was heated to reflux for 6 hours. The reaction was monitored by TLC. After the reaction was completed, the reaction mixture was cooled to room temperature. The organic layer was separated, and the water layer was extracted with 50 ml×4 of ethyl acetate. The organic layer was combined and was washed with saturated brine, and then was dried over anhydrous magnesium sulfate. The solvent was removed by rotary evaporator partially and then cooled to get crude product. The crude product was recrystallized from petroleum ether to give 2.6 grams of yellowish crystalline solid in a yield of 68.6%. $^1$H-NMR (ppm) δ: 7.08 (d, 1H, 2'-H), 6.92 (dd, 1H, 6'-H), 6.76 (d, 1H, 5'-H), 6.62 (s, 2H, 2,6-H), 6.49 (d, 1H, 1a-H), 6.43 (d, 1H, 1a'-H), 6.28 (t, 1H, $J^2_{H-F}$=72 Hz, —CHF$_2$), 5.13 (broad, 2H, NH$_2$), 3.86 (s, 3H, 4-OCH$_3$), 3.70 (s, 6H, 3,5-OCH$_3$).

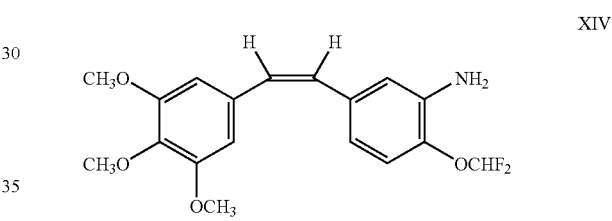

XIV

EXAMPLE 11

Synthesis of (Z)-1-(3,4,5-trimethoxyphenyl)-2-(3'-hydroxy-4'-trifluoroethoxyphenyl)-ethene (DD8031, formula XV)

Repeating example 9, except that 4-difluoromethoxy-3-hydroxybenzaldehyde was replaced with 14.5 grams (66 mmol) of 4-trifluoroethoxy-3-hydroxybenzaldehyde. After three steps reaction, (Z)-1-(3,4,5-trimethoxyphenyl)-2-(3'-hydroxy-4'-trifluoroethoxyphenyl)-ethene was obtained in a yield of 79.5%. $^1$H-NMR (ppm) δ: 6.93 (d, 1H, 2'-H), 6.84 (dd, 1H, 6'-H), 6.72 (d, 1H, 5'-H), 6.60 (s, 2H, 2,6-H), 6.45 (d, 1H, 1a-H), 6.38 (d, 1H, 1a'-H), 5.51 (broad, 1H, OH), 4.48 (2H, q, $J^3_{H-F}$=7.2 Hz, —CH$_2$CF$_3$), 3.86 (s, 3H, 4-OCH$_3$), 3.70 (s, 6H, 3,5-OCH$_3$).

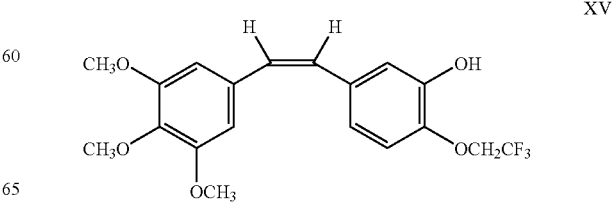

XV

EXAMPLE 12

Synthesis of (Z)-1-(3,4,5-trimethoxyphenyl)-2-(3'-amino-4'-trifluoroethoxyphenyl)-ethene (DD8041, formula XVI)

Repeating example 10, except that 4-difluoromethoxy-3-nitrobenzaldehyde was replaced with 14.5 grams (66 mmol) of 4-trifluoroethoxy-3-nitrobenzaldehyde. After two steps reaction, (Z)-1-(3,4,5-trimethoxy-phenyl)-2-(3'-amino-4'-trifluoroethoxyphenyl)-ethene was obtained in a yield of 43.6%. $^1$H-NMR (ppm) δ: 7.08 (d, 1H, 2'-H), 6.92 (dd, 1H, 6'-H), 6.76 (d, 1H, 5'-H), 6.62 (s, 2H, 2,6-H), 6.49 (d, 1H, 1a-H), 6.43 (d, 1H, 1a'-H), 5.13 (broad, 2H, $NH_2$), 4.40 (2H, q, $J^3_{H-F}$=7.2 Hz, —$CH_2CF_3$), 3.86 (s, 3H, 4-$OCH_3$), 3.70 (s, 6H, 3,5-$OCH_3$).

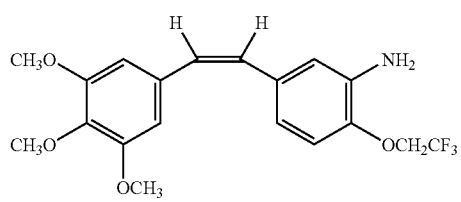

XVI

EXAMPLE 13

Synthesis of (Z)-1-(3,4,5-trimethoxyphenyl)-2-(3'-hydroxy-4'-difluoromethoxyphenyl)-ethene-3'-O-phosphate disodium salt (DD8011DP, formula XVII) and (Z)-1-(3,4,5-trimethoxyphenyl)-2-(3'-hydroxy-4'-trifluoroethoxyphenyl)-ethene-3'-O-phosphate disodium salt (DD8031DP, formula XVIII)

The process of the conversion of the hydroxy of combretastin A-4 to disodium phosphate water-soluble prodrug was disclosed in Pettit, G. R. et al., *Anti-Cancer Drug Design* 1998, 13, 183-191 (see FIG. 1 and FIG. 2).

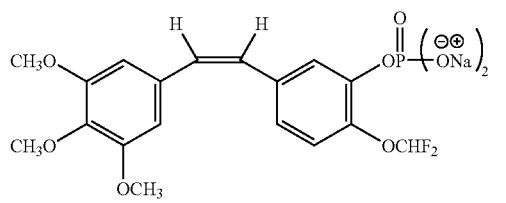

XVII

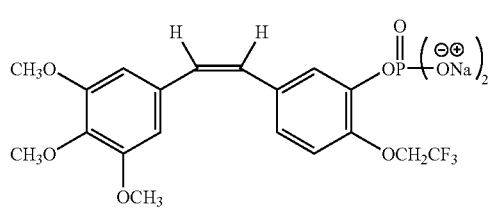

XVIII

EXAMPLE 14

Synthesis of (Z)-1-(3,4,5-trimethoxyphenyl)-2-(3'-amino-4'-difluoromethoxyphenyl)-ethene-3'-N-serinamide (DD8021AS, formula XIX) and (Z)-1-(3,4,5-trimethoxyphenyl)-2-(3'-amino-4'-trifluoroethoxyphenyl)-ethene-3'-N-serinamide (DD8041AS, formula XX)

Amino-substituted derivates of stilbene being reacted with N-α-9-fluorenylmethoxycarbonyl serine derivative (FmocAA) via coupling reaction, and then the resulting product was deprotected to give amino acid prodrug of stilbene compounds. The process was disclosed in Pettit, G. R. et al., *J. Med. Chem.*, 2002, 46, 525-31. See FIG. 3 and FIG. 4.

TABLE 1

| Formula No. | | $R_f$ | R |
|---|---|---|---|
| DD8011 | XIII | —$CHF_2$ | —OH |
| DD8021 | XIV | —$CHF_2$ | —$NH_2$ |
| DD8031 | XV | —$CH_2CF_3$ | —OH |
| DD8041 | XVI | —$CH_2CF_3$ | —$NH_2$ |
| DD8011DP | XVII | —$CHF_2$ | —$OPO_3Na_2$ |
| DD8031DP | XVIII | —$CH_2CF_3$ | —$OPO_3Na_2$ |
| DD8021AS | XIX | —$CHF_2$ | —$NHCOCH(NH_2)CH_2OH$ |
| DD8041AS | XX | —$CH_2CF_3$ | —$NHCOCH(NH_2)CH_2OH$ |

EXAMPLE 15

In Vitro Antitumor Activity Evaluation

The tumor cell cultured in vitro being administrated with fluoroalkoxycombretastatin for 72 hours, the MTT and SRB assays was used to evaluate its inhibition of tumor proliferation. The comparative result with CA-4 was shown in Table 2.

Cell groups: H460 human lung cancer cell, SGC7901: human stomach cancer cell, HT-29 human colon cancer cell, Bel-7402 human liver cancer cell.

Experiment design: cells were warm-cultured with the compounds in different concentrations (100, 10, 1, 0.1, 0.01, 0.001 μM) for 72 hours. SRB assay was used to evaluate the inhibition degree of the compounds to cell proliferation. The inhibition rate was calculated, and $IC_{50}$ was calculated by using Logit model according to the inhibition rate. And the antitumor activity of compounds in vitro was compared.

The inhibition rate was expressed using the following equation:

Inhibition rate (%)=[(average OD value of control group−average OD value of experimental group)/average OD value of control group]×100%.

TABLE 2

| Comd. | IC$_{50}$(μM) | | | |
|---|---|---|---|---|
| | Stomach cancer SGC-7901 | Non-small cell lung cancer H460 | Colon cancer HT29 | Liver cancer Bel-7402 |
| CA-4 | 0.010 | 0.027 | 2.380 | 0.75 |
| DD8011 | 0.022 | 0.044 | 3.000 | 0.92 |
| DD8021 | 0.018 | 0.036 | 2.250 | 0.83 |
| DD8031 | 0.005 | 0.005 | 0.079 | 0.30 |
| DD8041 | 0.003 | 0.005 | 0.068 | 0.28 |

The result showed that fluromethoxycombretastain had similar anti-tumor activity in vitro with that of natural combretastatin A-4. While the fluoroethoxycombrestastin had 3 to 30 folds of anti-tumor activity than that of fluoromethoxycombretastatin.

EXAMPLE 16

In Vitro Neovascular Inhibition Evaluation

Anti-angiogenesis effects of fluoroalkoxycombretastatins were assessed in human umbilical vein endothelial cells (HU-VEC) using the same method in Example 15.

TABLE 3

| Comd. | IC$_{50}$(μM) HUVEC |
|---|---|
| CA-4 | 0.003 |
| DD8011 | 0.002 |
| DD8021 | 0.002 |
| DD8031 | 0.001 |
| DD8041 | 0.001 |

The result showed that fluoroalkoxycombretastatins had strong tubulin-binding inhibition activity, and indicated that fluoroalkoxycombretastatins were a new class of the potential tumor vascular targeting drugs. (Table 3)

EXAMPLE 17

Preparation of Fluoroalkoxycombretastatin Freeze-Dried Powder

TABLE 4

| Formula | Content(g) |
|---|---|
| DD8031DP | 25 |
| Mannitol | 125 |
| Injection water | 2500 |
| DD8031DP freez-dried powder | 0.025/bottle × 1000 bottle |

Materials were weighed exactly according to the formulas (Table 4). Formula amount of mannitol was dissolved in 80% formula amount of injection water to give a clarity solution, and 0.1% (g/ml) injection coke was added. The mixture was stirred and settled and filtered through 0.45 μm micro-hole membrane and the rest injection water was added. The solution was filtered again through 0.22 μm micro-hole membrane. pH value and content were measured to give the qualified product. And then the solution was filled into bottle in certain quantity and then was freeze dried. Nitrogen was introduced and then was stopped and labeled, boxed, and proof-tested to give finished product (because the derivatives of Combretastatin is moderately sensitive to temperature and light, so the whole operation processes were done in dark condition and the finished products were stored at 2-8° C. in the dark.).

All the documents cited herein are incorporated into the invention as reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed is:

1. A compound of formula (I)

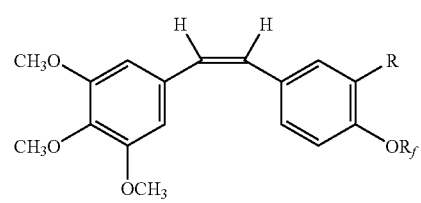

wherein R$_f$ is an alkyl group having 1 to 8 carbon atoms in which 1 to 17 hydrogen atoms being substituted by 1 to 17 fluorine atoms;
R is amino, substituted amino, hydroxyl, nitro, halogen, alkoxy, phosphate or side chain of a nature amino acid and its pharmaceutically acceptable salts.

2. The compound of claim 1, wherein R$_f$ and R are selected from the following groups:
(a) R$_f$ is fluoromethyl, R is hydroxyl;
(b) R$_f$ is fluoromethyl, R is amino or substituted amino;
(c) R$_f$ is fluoromethyl, R is disodium phosphate or ammonium phosphate; or
(d) R$_f$ is fluoromethyl, R is —NH(COCHR'NH)$_m$—H, R' is hydrogen, phenyl, m is an integer of 1 to 3.

3. The compound of claim 1, wherein R$_f$ and R are selected from the following groups:
(a) R$_f$ is fluoroethyl, R is hydroxyl;
(b) R$_f$ is fluoroethyl, R is amino or substituted amino;
(c) R$_f$ is fluoroethyl, R is disodium phosphate or ammonium phosphate; or
(d) R$_f$ is fluoroethyl, R is —NH(COCHR'NH)$_m$—H, R' is hydrogen, side chain of a nature amino acid, phenyl, m is an integer of 1 to 3.

4. The compound of claim 1, wherein R$_f$ and R are selected from the following groups:
(a) R$_f$=—CH$_2$F, —CHF$_2$, —CF$_3$, —CH$_2$CF$_3$, —CH$_2$CHF$_2$ or —CF$_2$CF$_3$, R=—OH or —OPO$_3$Na$_2$; or
(b) R$_f$=—CH$_2$F, —CHF$_2$, —CF$_3$, —CH$_2$CF$_3$, —CH$_2$CHF$_2$ or —CF$_2$CF$_3$, R=—NH$_2$ or —NHCOCH(NH$_2$)CH$_2$OH.

5. A method for preparing the compound in accordance with claim 1, comprising the steps of:
(1) under phase-transfer catalyst conditions, 4-hydroxy-3-methoxybenzaldehyde III being fluoroalkoxylated with fluorine-containing reagent to synthesize 4-fluoroalkoxy-3-methoxybenzaldehyde represented by formula V;

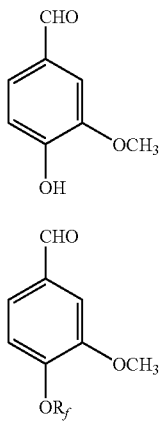

III

V (2) using lithium diphenylphosphine, 4-fluoroalkoxy-3-methoxybenzaldehyde being demethylated to synthesize 4-fluoroalkoxy-3-hydroxybenzaldehyde represented by formula VI;

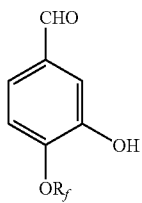

VI (3) the hydroxyl of 4-fluoroalkoxy-3-hydroxybenzaldehyde VI being protected, and then reacted with 3,4,5-trimethoxybenzyltriphenylphosphonium ylid via Wittig reaction, and the resulted compound being released from protection to obtain the compound of formula I in accordance with claim 1.

6. A method for preparing the compound in accordance with claim 1, comprising the steps of:

(a) under phase-transfer catalyst conditions, 4-hydroxybenzaldehyde IV being fluoroalkylated with fluorine-containing reagent to synthesize 4-fluoroalkoxybenzaldehyde represented by formula VII;

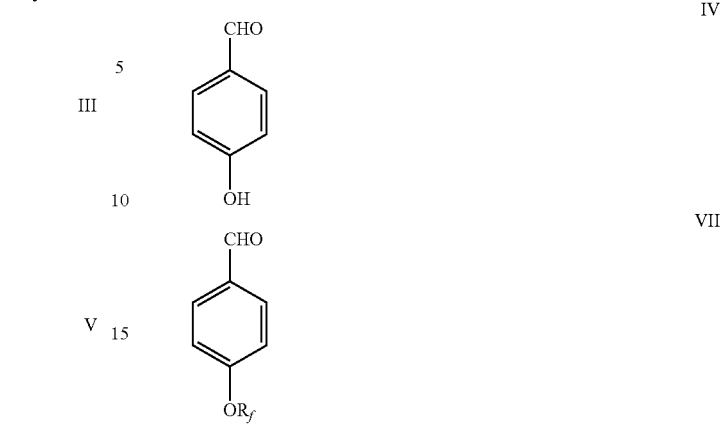

IV

VII (b) 4-Fluoroalkoxybenzaldehyde VII being nitrated in 3 position of phenyl ring with nitric acid and acetic anhydride to synthesize 4-fluoroalkoxy-3-nitrobenzaldehyde, which is represented by formula VIII;

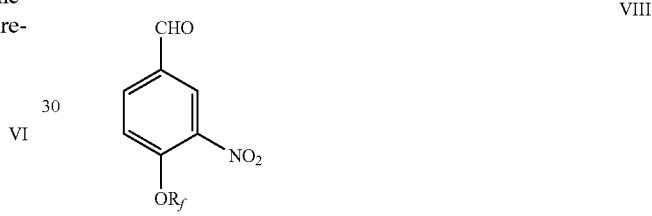

VIII (c) 4-fluoroalkoxy-3-nitrobenzaldehyde VIII being reacted with 3,4,5-trimethoxybenzyltriphenylphosphine ylid via Wittig reaction to obtain the compounds of formula I in accordance with claim 1.

7. The method of claim 5, wherein the fluorine-containing reagent is fluorohalomethane or fluoroalkyl sulphonate.

8. A pharmaceutical composition comprising the compound in accordance with claim 1 or a pharmaceutically acceptable salt thereof in a therapeutic effective dosage and a pharmaceutically acceptable carrier.

9. A method of treatment of patients with stomach cancer, non-small cell lung cancer, colon cancer, and liver cancer, comprising administering an effective amount to said patient of the compound in accordance with claim 1 or a pharmaceutically acceptable salt thereof.

10. The method of claim 6, wherein the fluorine-containing reagent is fluorohalomethane or fluoroalkyl sulphonate.

* * * * *